US011694326B2

United States Patent
Pala (10) Patent No.: US 11,694,326 B2
(45) Date of Patent: Jul. 4, 2023

(54) SYSTEM AND METHOD FOR PROCESSING A DIAGNOSTIC TEST ARTICLE

(71) Applicant: Clinical Reference Laboratory, Inc., Lenexa, KS (US)

(72) Inventor: Serhat Pala, San Diego, CA (US)

(73) Assignee: Clinical Reference Laboratory, Inc., Lenexa, KS (US)

( * ) Notice: Subject to any disclaimer, the term of this patent is extended or adjusted under 35 U.S.C. 154(b) by 359 days.

(21) Appl. No.: 17/011,714

(22) Filed: Sep. 3, 2020

(65) Prior Publication Data

US 2021/0065346 A1 Mar. 4, 2021

Related U.S. Application Data

(60) Provisional application No. 62/962,511, filed on Jan. 17, 2020, provisional application No. 62/895,373, filed on Sep. 3, 2019.

(51) Int. Cl.
| | | |
|---|---|---|
| G06T 7/00 | (2017.01) | |
| G16H 50/20 | (2018.01) | |
| G16H 30/40 | (2018.01) | |
| G06K 7/14 | (2006.01) | |
| G16H 10/40 | (2018.01) | |
| H04L 67/01 | (2022.01) | |
| H04W 4/90 | (2018.01) | |
| H04B 1/3827 | (2015.01) | |

(52) U.S. Cl.
CPC ............ *G06T 7/001* (2013.01); *G06K 7/1413* (2013.01); *G16H 10/40* (2018.01); *G16H 30/40* (2018.01); *G16H 50/20* (2018.01); *H04L 67/01* (2022.05); *G06T 2207/30004* (2013.01); *H04B 1/3827* (2013.01); *H04W 4/90* (2018.02)

(58) Field of Classification Search
CPC . G06T 7/001; G06T 7/00; G06T 2207/30004; G16H 50/20; G16H 30/40; G16H 10/40; G06K 7/14; G06K 7/143; H04L 67/01; H04L 67/42; H04L 29/06; H04B 1/3827
See application file for complete search history.

(56) References Cited

U.S. PATENT DOCUMENTS

| | | | | |
|---|---|---|---|---|
| 2016/0005183 A1* | 1/2016 | Thiagarajan | ........... | G06T 7/0012 382/131 |
| 2019/0034630 A1* | 1/2019 | Khatri | ..................... | G06F 21/56 |

* cited by examiner

*Primary Examiner* — Tuan H Nguyen
(74) *Attorney, Agent, or Firm* — CP Law Group PC; Cy Bates (57) ABSTRACT

A system and related methods are provided for processing a diagnostic test article, for example, one that is used for medical or substance testing. The system and methods combine a diagnostic test article with a software application that is integrated with each of a mobile communication device and a cloud-based network via an internet connection for achieving certain advantages and improvements over conventional point of use diagnostics.

19 Claims, 6 Drawing Sheets

Method for Processing a Diagnostic Test Article

Selecting a diagnostic test article type from a plurality of possible diagnostic test article types Identifying a diagnostic test article and at least one result strip associated with the diagnostic test article, and verifying the diagnostic test article matches the selected diagnostic test article type Performing a diagnostic test by:

Collecting a biological sample; and
Delivering the biological sample to a test-chamber of the diagnostic test article; wherein upon receiving the biological sample, the diagnostic test article is configured to provide results of an analyte test at each of the at least one diagnostic strip associated with the diagnostic test article Characterizing the results of each analyte test at each of the at least one diagnostic strip associated with the diagnostic test article

FIG.3

Method for Processing a Diagnostic Test Article (i) identifying a diagnostic test article type from a plurality of possible diagnostic test article types, the diagnostic test article being one of the diagnostic test article types, wherein the diagnostic test article type is associated with characteristic information including: number of diagnostic panels of the diagnostic test article type and number of diagnostic strips for each of the diagnostic panels (ii) characterizing results of a diagnostic test using the diagnostic test article, wherein said characterizing results comprises:

acquiring one or more results images, each of the results images corresponding to one of the diagnostic panels of the diagnostic test article after completing a diagnostic test using the diagnostic test article, comparing each of the one or more results images to a plurality of source images of an image dataset, the source images of the image dataset being stored on one or more network servers, and for each of the diagnostic strips of the diagnostic panels of the diagnostic test article, receiving from the one or more network servers an automated value based on said comparing, wherein the automated value corresponds to one of: 'positive', 'negative', or 'null'

SYSTEM AND METHOD FOR PROCESSING A DIAGNOSTIC TEST ARTICLE

CROSS-REFERENCE TO RELATED APPLICATION

This application claims benefit of priority with U.S. provisional application Ser. No. 62/895,373, filed Sep. 3, 2019; and further claims benefit of priority with U.S. provisional application Ser. No. 62/962,511, filed Jan. 17, 2020; the entire contents of each of which is hereby incorporated by reference.

TECHNICAL FIELD

This invention relates to systems and methods for processing diagnostic test articles; and more particularly, to such systems and methods incorporating software applications and machine automation for determining, storing, and sharing results of a diagnostic test.

BACKGROUND ART

Diagnostic test articles are conventionally used in the art of medical and substance-related testing, for example and not limitation, drug testing.

Currently, a diagnostic test article is provided to a subject and administered either by the subject or by a clinician, and results may be provided as an instant test or as a laboratory test, the instant test providing immediate results to the subject and/or clinician.

With the advent of computer technologies, such as smart phones and the like, there are now opportunities to access vast amounts of data via an internet connection. The data may take the form of photographic images or other data. Additionally, machine learning techniques have been developed for providing image analysis and automation in many fields.

SUMMARY OF INVENTION

Technical Problems

Currently, there is no available system and method for providing point of use diagnostic testing using a diagnostic test article that achieves instant results and provides concurrently ability to confirm the instant results by laboratory analysis.

There is no available system and method providing instant results to a subject and/or clinician as well as a remotely located customer (e.g. company management for hiring decisions, law enforcement personnel, and the like).

There is no available system and method that accomplishes the forgoing and concurrently deters the subject from tampering with the diagnostic test article and/or misrepresenting the subject identity (e.g. using another's urine or saliva during the diagnostic test).

There is a need to reduce human involvement while maintaining safeguards for test precision and accuracy, for example, by reducing human involvement by selectively eliminating laboratory confirmation for one or more diagnostic tests.

There is a need to store records associated with diagnostic tests in a remote, backed up and secure cloud storage system, and providing access to the same.

Other technical problems will be recognized by one having skill in the art.

Solutions to Problems

In various embodiments, a system and methods are provided for processing a diagnostic test article. The system and methods integrate a diagnostic test article with a software application that is integrated with each of a mobile communication device and a cloud-based network via an internet connection for achieving certain advantages and improvements over conventional point of use diagnostics.

Advantageous Effects of Invention

The system and methods disclosed herein provide point of use diagnostic testing for use by a remote subject and/or clinician, the system and methods integrate a diagnostic test article and a software application, the combination of which provides instant results to each of the subject and/or clinician as well as, optionally, a remotely located customer, and provides an ability to confirm the instant results by laboratory analysis.

The system and methods are adapted to deter the subject from tampering with the diagnostic test article and/or misrepresenting the subject identity (e.g. using another's urine or saliva during the diagnostic test). This is generally accomplished by requiring all diagnostic test articles to be mailed to a laboratory, where optional laboratory testing, such as results confirmation or subject identification can be completed.

The system and methods can reduce human involvement while maintaining safeguards for test precision and accuracy, for example, with respect to reducing human involvement, by selectively eliminating laboratory confirmation for one or more diagnostic tests. The customer (company, law enforcement agency, and the like) can elect to process the diagnostic test article that is received from the subject using further laboratory processing, or may alternatively decide to accept the instant results.

The system and methods are capable of storing medical and substance diagnostic records on a cloud-based network for access at one of a plurality of remote locations.

Other advantageous effects of the invention will be recognized by one having skill in the art upon a review of the instant disclosure.

BRIEF DESCRIPTION OF DRAWINGS

The detailed description is described with reference to the accompanying figures. The use of the same reference numbers in different instances in the description and the figures may indicate similar or identical items. Various embodiments or examples ("examples") of the present disclosure are disclosed in the following detailed description and the accompanying drawings. The drawings are not necessarily to scale. In general, operations of disclosed processes may be performed in an arbitrary order, unless otherwise provided in the claims.

DESCRIPTION OF EMBODIMENTS

For purposes of explanation and not limitation, details and descriptions of certain preferred embodiments are hereinafter provided such that one having ordinary skill in the art may be enabled to make and use the invention. These details and descriptions are representative only of certain preferred embodiments, however, and a myriad of other embodiments which will not be expressly described will be readily understood by one having skill in the art upon a thorough review of the instant disclosure. Accordingly, any reviewer of the instant disclosure should interpret the scope of the invention only by the claims, as such scope is not intended to be limited by the embodiments described and illustrated herein.

EXAMPLES

The invention can be practiced in accordance with a number of examples, including those as illustrated herein, or otherwise as would be appreciated by one having skill in the art.

For purposes herein, unless a term used to describe the invention is expressly defined it should be understood that the plain and ordinary meaning for that term should apply, and if there is a discrepancy as to the plain and ordinary meaning of that term, then the definition as would be appreciated by one having skill in the art shall apply.

Example 1—System for Processing a Diagnostic Test Article

In a first example, a system for processing a diagnostic test article is provided. The system generally comprises each of a customer side, a client side and a server side connected to internet via one of a plurality of internet connections. The customer side includes at least one customer access device. The client side includes a mobile communication device and a client application integrated with the mobile communication device. The server side includes one or more network servers configured to access an image dataset, the image dataset comprising a plurality of source images.

The system is further characterized in that with the client application, the mobile communication device is configured to execute a series of steps for processing the diagnostic test article, the steps comprising in order: (i) identifying a diagnostic test article type from a plurality of possible diagnostic test article types, the diagnostic test article being one of the diagnostic test article types, wherein the diagnostic test article type is associated with characteristic information including: number of diagnostic panels of the diagnostic test article type and number of diagnostic strips for each of the diagnostic panels; and (ii) characterizing results of a diagnostic test using the diagnostic test article. The step of characterizing results may comprise: (i) acquiring one or more results images, each of the results images corresponding to one of the diagnostic panels of the diagnostic test article, (ii) comparing each of the one or more results images to a plurality of the source images of the image dataset, and for each of the diagnostic strips of the diagnostic panels of the diagnostic test article, (iii) assigning an automated value based on said comparing, wherein the automated value corresponds to one of: 'positive', 'negative', or 'null'.

In some embodiments, the client application can be integrated with the mobile communication device via the internet.

In some embodiments, the client application can be integrated with the mobile communication device via memory housed on the mobile communication device.

In some embodiments, the server side can be configured to store a plurality of client records on the one or more network servers, each client record individually comprising test information, wherein the test information may include, without limitation: the diagnostic test article type, the characteristic information, the automated value for each of the diagnostic strips of the diagnostic panels of the diagnostic test article, the one or more results images, and optionally a client-provided value (which may include a "manually-changed value" or a "confirmed value") for one or more of the diagnostic strips of the diagnostic panels. The system may further comprise a customer application integrated with the at least one customer access device, wherein the customer application is configured to access the test information associated with one or more of the client records stored on the networks servers. The customer application can be integrated with the at least one customer access device via the internet.

In some embodiments, the customer application can be integrated with the at least one customer access device via memory housed on the at least one customer access device.

In various embodiments, the mobile communication device may comprise a smart phone or tablet computer, or other portable device that may be appreciated by one having skill in the art.

In some embodiments, one or more customer access device(s) can be configured to access the automated value and/or manually-changed value from the one or more network servers, in particular if the customer access device(s) have authorization, for example, by way of account association and login, in order to view results of a particular diagnostic test.

Figure 1:
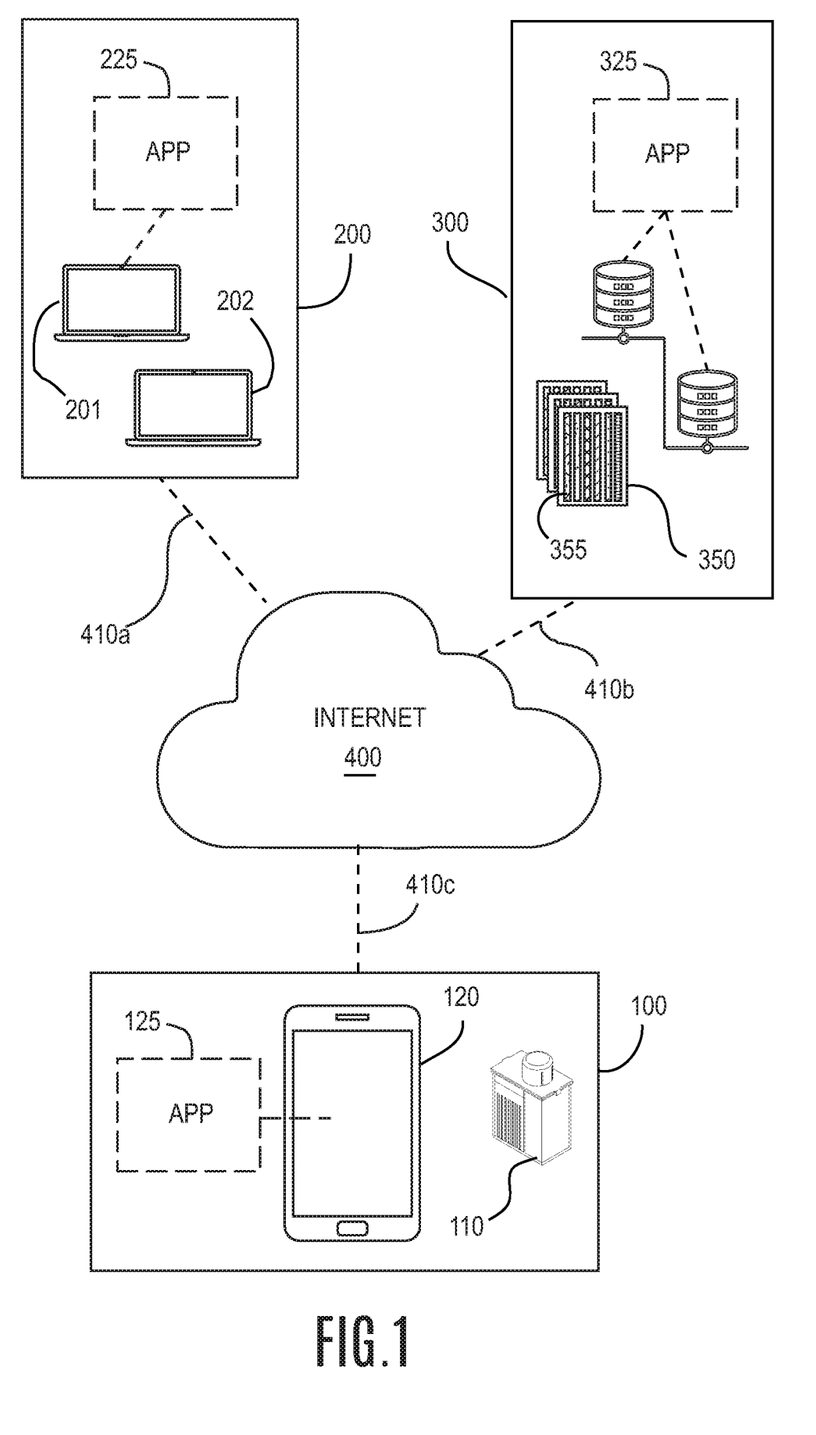
FIG. 1 shows a schematic representation of a system for processing a diagnostic test article using a software application integrated with each of a mobile communication device and one or more network servers remotely disposed on a network infrastructure via an internet connection.

Now turning to FIG. 1, which shows a schematic representation of a system for processing a diagnostic test article using a software application integrated with each of a mobile communication device and one or more network servers remotely disposed on a network infrastructure via an internet connection.

Here, the system comprises a client side (100) coupled to each of a customer side (200) and a server side (300) via the internet (400) and one or more internet connections (410a; 410b; 410c), respectively.

On the client side is a diagnostic test article (110) configured with one or more diagnostic panels, each diagnostic panel being positioned on one side of the diagnostic test article and further comprising a plurality of diagnostic strips, wherein each diagnostic strip is configured to test for one of a plurality of possible analytes, for example and not limitation, illicit drug analytes, medical condition-associated biomarkers, and the like or as would be appreciated by one having skill in the art. For example and not limitation, the diagnostic test article may comprise a first panel on a first side, and a second panel on a second side, wherein multiple diagnostic strips can be tested from a common biological sample, and multiple images of the multiple corresponding panels may be similarly considered in the process.

Also, on the client side is a mobile communication device (120). The mobile communication device may comprise a smart phone with camera, a tablet personal computer, or other portable electronic device having a camera and being configured to access other devices through a network connection.

The mobile communication device may comprise a processor coupled to non-transient computer readable memory, wherein a software application (125) is stored on the memory. The mobile communication device and software application can be configured to connect to the one or more network servers of the network via the one or more internet connections.

Alternatively, the software application may span a combination of the mobile communication device and one or more network servers on the network; for example, the network servers can house a server-portion (325) of the software application. Additionally, or alternatively, the software application may span the mobile communication device and one or more customer access devices (201; 202) coupled to the network; for example, the customer access devices can house a customer-portion (225) of the software application. In this regard, a portion of the software application is stored on the mobile communication device whereas another portion is stored on the customer access device(s) and/or the one or more network servers.

On the server side of the network, the system comprises one or more network servers (301; 302) connected to the internet. Each of the one or more network servers may individually comprise a plurality of source images (350). The source images are generally images that taken together form an image dataset, wherein each image of the image dataset contains an image of a results panel (355) of a diagnostic test article. For purposes herein, a results panel is a diagnostic panel that has been used to test the presence or absence of analyte from a specimen, such as but not limited to saliva or urine of a subject being tested. Each of the plurality of source images is stored on the one or more network servers as the image dataset, and the image dataset is accessible for the purpose of comparing a results image (i.e. an image associated with a particular diagnostic test article that is under assessment using the system and methods herein) and assigning an automated value of the result for each analyte being tested.

The image dataset can be configured to continuously evolve with the addition of a results image, thereby enhancing the image dataset with new image data after each diagnostic test is processed using the system. Thus, the system is adapted for machine learning for improving precision and accuracy used to assess individual analyte results for each results panel of each diagnostic testing article reviewed by the system.

Example 2—Method for Processing a Diagnostic Test Article with a Mobile Communication Device In another example, a method for processing a diagnostic test article is provided. The method generally comprises: using a client application integrated with a mobile communication device, the steps of: (i) identifying a diagnostic test article type from a plurality of possible diagnostic test article types, the diagnostic test article being one of the diagnostic test article types, wherein the diagnostic test article type is associated with characteristic information including: number of diagnostic panels of the diagnostic test article type and number of diagnostic strips for each of the diagnostic panels; and (ii) characterizing results of a diagnostic test using the diagnostic test article. The step of 'characterizing results' may comprise: (i) acquiring one or more results images, each of the results images corresponding to one of the diagnostic panels of the diagnostic test article after completing a diagnostic test using the diagnostic test article, (ii) comparing each of the one or more results images to a plurality of source images of an image dataset, the source images of the image dataset being stored on one or more network servers, and (iii) for each of the diagnostic strips of the diagnostic panels of the diagnostic test article, (iv) receiving from the one or more network servers an automated value based on said comparing, wherein the automated value corresponds to one of: 'positive', 'negative', or 'null'.

For purposes herein, the phrase 'using a client application integrated with the mobile communication device' may comprise opening the client application from memory housed on the mobile communication device. In some but not all embodiments, the method may be further distinguished in that at least a portion of the client application can be stored on the one or more network servers, wherein said using a client application integrated with the mobile communication device comprises opening the client application in combination with the one or more network servers and the mobile communication device via an internet connection.

In some embodiments, the step of 'identifying the diagnostic test article type' may comprise inputting typographical characters into the client application.

In other embodiments, the step of 'identifying the diagnostic test article type' may comprise using the mobile communication device, scanning a barcode coupled to the diagnostic test article, wherein the barcode contains information relating the diagnostic test article and its corresponding diagnostic test article type.

In other embodiments, the step of 'identifying the diagnostic test article type' may comprise: using the mobile communication device, acquiring one or more panel images of the diagnostic test article, of each panel images corresponding to one of the one or more of the diagnostic panels of the diagnostic test article, comparing the one or more panel images to up to each of the plurality of source images of the image dataset, assigning the diagnostic test article type from a plurality of possible diagnostic test article types, and returning the diagnostic test article type to the mobile communication device.

In other embodiments, the step of 'identifying the diagnostic test article type' may comprise using near-field-communication of the mobile communication device, reading a radiofrequency identification tag coupled to the diagnostic test article.

Figure 2:
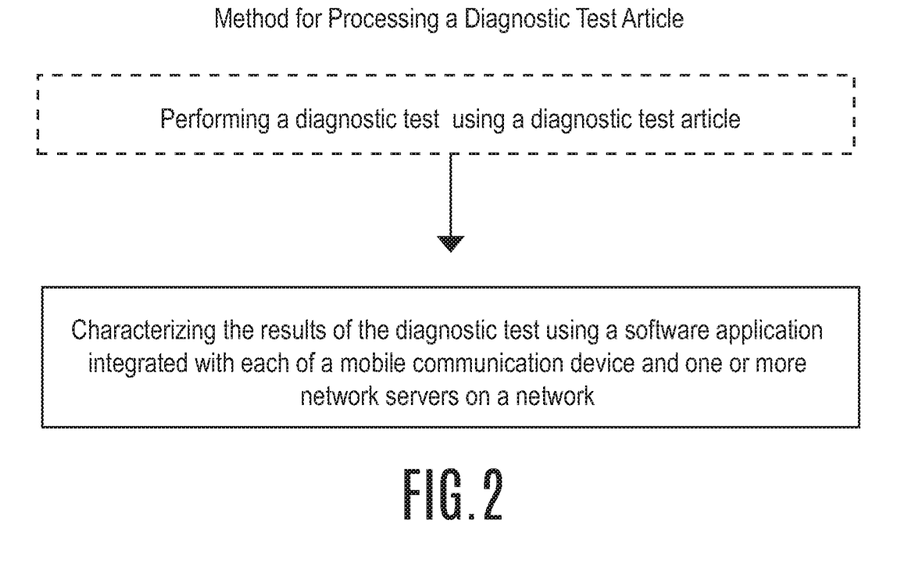
FIG. 2 shows a method for processing a diagnostic test article on a client side of the network infrastructure as shown in FIG. 1 in accordance with an embodiment.

With reference to FIG. 2, a method for processing a diagnostic test article on a client side of the network infrastructure is shown. The network infrastructure can be one as illustrated in FIG. 1 or otherwise as would be appreciated by one having skill in the art.

With reference to FIG. 2, the method for processing a diagnostic test article comprises: (i) performing a diagnostic test using a diagnostic test article (this step involves human-directed actions and is shown in broken lines as not forming part of the method as would be performed by the software application, but is a related step associated with the method for processing a diagnostic test article; and (ii) characterizing the results of the diagnostic test using a software application integrated with each of a mobile communication device and one or more network servers on a network.

Figure 3:
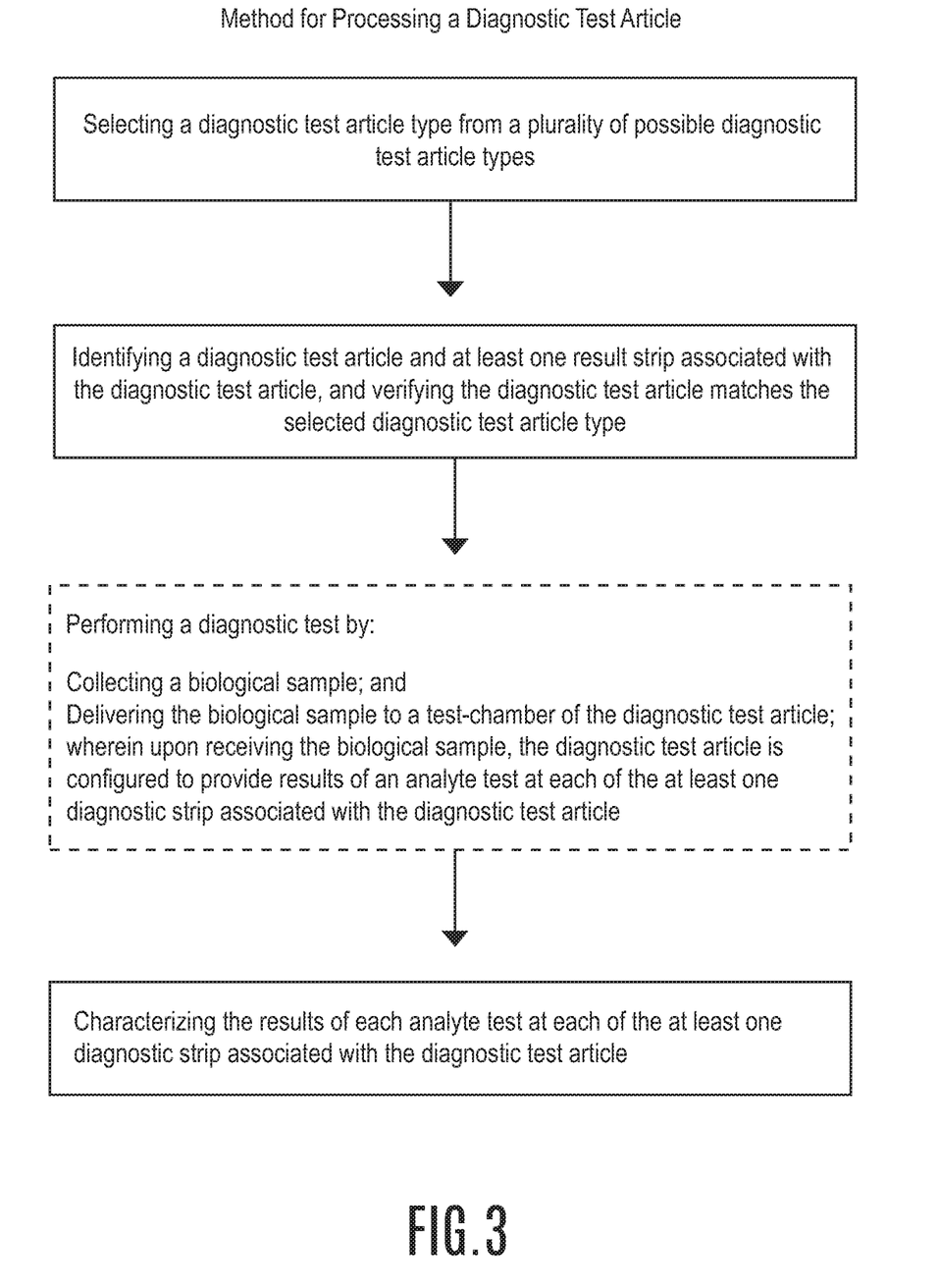
FIG. 3 shows a method for processing a diagnostic test article on a client side of the network infrastructure as shown in FIG. 1 in accordance with another embodiment.

For example, the method as illustrated in FIG. 3 further details a particular embodiment of FIG. 2, wherein the method for processing a diagnostic article on a client side of the network infrastructure comprises: (i) selecting a diagnostic test article type from a plurality of possible diagnostic test article types; (ii) identifying a diagnostic test article and at least one result strip associated with the diagnostic test article, and verifying the diagnostic test article matches the selected diagnostic test article type; (iii) performing a diagnostic test by: collecting a biological sample, and delivering the biological sample to a test-chamber of the diagnostic test article, wherein upon receiving the biological sample, the diagnostic test article is configured to provide results of an analyte test at each of the at least one diagnostic strips associated with the diagnostic test article; and (iv) characterizing the results of each analyte test at each of the at least one diagnostic strips associated with the diagnostic test article.

Figure 4:
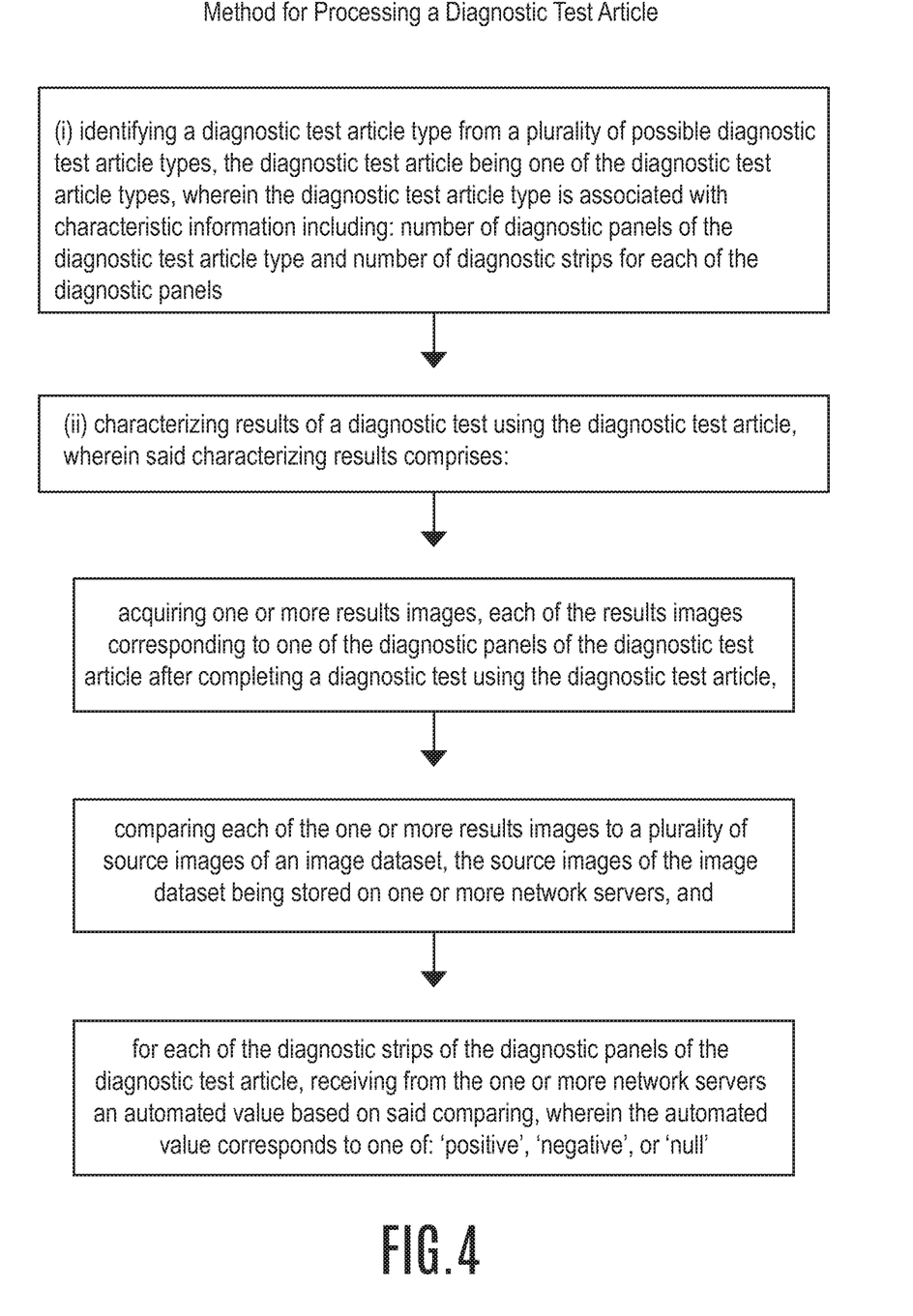
FIG. 4 shows a method for processing a diagnostic test article on a client side of the network infrastructure as shown in FIG. 1 in accordance with another embodiment.

FIG. 4 shows a method for processing a diagnostic test article on a client side of the network infrastructure in accordance with another embodiment. The method may comprise the steps of, using a client application integrated with a mobile communication device: (i) identifying a diagnostic test article type from a plurality of possible diagnostic test article types, the diagnostic test article being one of the diagnostic test article types, wherein the diagnostic test article type is associated with characteristic information including: number of diagnostic panels of the diagnostic test article type and number of diagnostic strips for each of the diagnostic panels; and (ii) characterizing results of a diagnostic test using the diagnostic test article, wherein said characterizing results comprises: acquiring one or more results images, each of the results images corresponding to one of the diagnostic panels of the diagnostic test article after completing a diagnostic test using the diagnostic test article, comparing each of the one or more results images to a plurality of source images of an image dataset, the source images of the image dataset being stored on one or more network servers, and for each of the diagnostic strips of the diagnostic panels of the diagnostic test article, receiving from the one or more network servers an automated value based on said comparing, wherein the automated value corresponds to one of: 'positive', 'negative', or 'null'.

Figure 5:
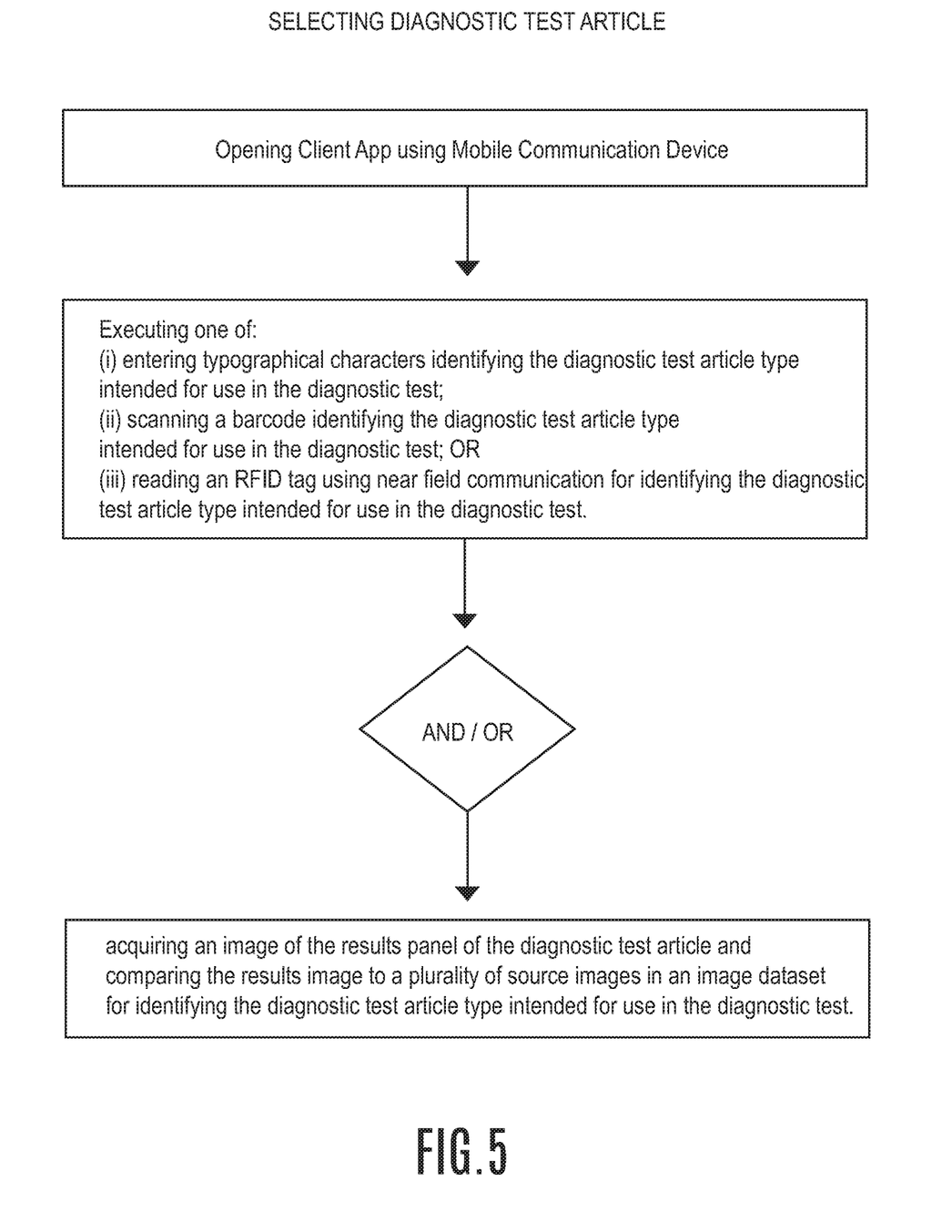
FIG. 5 shows a process for selecting a diagnostic test article for use with any of the methods of FIGS. 2-4.

FIG. 5 shows a process for selecting a diagnostic test article for use with any of the methods of FIGS. 2-4. Here, the process may begin with the step of opening the client application using the mobile communication device, executing one of: (i) entering typographical characters identifying the diagnostic test article type intended for use in the diagnostic test; (ii) scanning a barcode identifying the diagnostic test article type intended for use in the diagnostic test; or (iii) reading a radiofrequency identification (RFID) tag using near field communication of the mobile communication device for identifying the diagnostic test article type intended for use in the diagnostic test; and additionally or alternatively (iv) acquiring a results image of the results panel of the diagnostic test article (after performing a diagnostic test) and comparing the results image to a plurality of source images in an image dataset for identifying the diagnostic test article type intended for use in the diagnostic test.

For purposes herein, a point of use test, or instant test, generally comprises a collection device suitable for collecting a biological sample, such as urine, saliva and the like, and containing the biological sample in a sample well. The biological sample, when disposed in the sample well, is configured to contact a plurality of diagnostic strips (a.k.a. results strips), such that the biological sample is absorbed into each of the diagnostic strips where it may interact with an indicator. Upon contacting the indicator, a color change may occur, for example, where a specific analyte that corresponds to the indicator is present in the biological sample. In this regard, after completion of a diagnostic test using the diagnostic test article, each of the diagnostic strips may be observed for colorimetric identification and assessing the presence or absence of each analyte tested. While this has been traditionally accomplished via human interaction and interpretation, the embodiments of the invention provide for automated recognition of diagnostic test results, among other things.

For purposes herein, machine learning generally includes the construction or generation of machine learning algorithms that can learn from data. These algorithms are used to build a model based on features that is used to generate a classifier tuned to a particular purpose. Active machine learning is a discipline where a "teacher," such as a user, presents training examples to train a function to the model. Historically, whether training examples were labeled or unlabeled has been based on the particular purpose. Machine learning necessitates relatively high-quality labeled training examples such that the model can adequately learn the desired function for future classification of any number of unlabeled input documents. However, the discovery of high-quality labeled training examples amongst the virtually unlimited number of unlabeled documents available to the machine learning algorithm is typically costly. For example, many users are employed to interpret unlabeled documents to determine viability for machine learning purposes. However, if a particular model being trained by existing machine learning algorithms needs to be limited, the viability of each potential candidate for a labeled training example must be even more carefully considered, and costs can exceed desired targets.

The system and methods herein may implement machine learning for purposes of enhancing the image dataset. For example, a diagnostic test article can be utilized with a positive biological sample, such that a positive result may be presented at one of the diagnostic strips of a diagnostic panel. With this positive read, a video may be acquired, the video comprising a plurality of image frames over a period of time, wherein the video can be acquired in varied lighting and/or from various perspectives and/or distances. In this regard, a large number of varied images of the same positive read can be acquired in a single video file, and parsed accordingly. The large number of images become the initial source images of the image dataset. After which, as additional tests are performed and classified as positive for the respective analyte being tested, those tests, by and through their corresponding images, can be added to the image dataset thereby enhancing the image dataset for subsequent use. The image dataset may be continuously improved by the addition of source images. In this regard, whether the results image of a particular diagnostic test is acquired with a particular lighting or from a particular perspective, the plurality of source images will serve to allow the system to assess an automated result, wherein the automated result further characterizes the respective image or portion of an image as being a positive, negative or null result.

Therefore, for example and not limitation, when taking a picture, a first machine learning attribute will first detect if an image is one of an instant test kit and then crop the image to only the unique diagnostic strips. If the collector (e.g. subject or clinician) is testing a kit (diagnostic test article) with five diagnostic strips, the first attribute will crop the image and make sure that five diagnostic strips are present. If some number other than five strips are detected, the first attribute will know there is not a match and prompt the collector to either retake the picture or try again with the correct diagnostic test article. This process allows the collector to use the mobile communication device camera to take pictures rather than having to align each strip into an onscreen template which can be burdensome. Once the image is cropped, it is passed to the second attribute of the machine learning process. This is where the diagnostic strips are interpreted as a result. If two red lines are detected, the result is negative. If one top line is present, the result is positive and if one bottom line is present, the result is invalid. As more pictures are taken, more accuracy builds into the machine learning process. Once diagnostic strips are detected, the system can be taught to teach in how to read each strip differently. So, if the diagnostic panel has two diagnostic strips, such as two drugs, and different reading mechanism, then machine learning can be done to read it accordingly.

Example 2—Method for Processing a Diagnostic Test Article with a Mobile Communication Device In another example, a method for processing a diagnostic test article is provided. The method generally comprises: with one or more network servers connected to a mobile communication device via an internet connection, the steps of: (i) receiving one or more results images from the mobile communication device; (ii) comparing the results images to a plurality of source images of an image dataset, the source images of the image dataset being stored on the one or more network servers; (iii) assigning an automated value based on said comparing, wherein the automated value corresponds to one of: 'positive', 'negative', or 'null', and (iv) returning the automated value to the mobile communication device.

In some embodiments, the method may further comprise the steps: (i) receiving from the mobile communication device one or more panel images of the diagnostic test article, each of the panel images corresponding to one of one or more diagnostic panels of the diagnostic test article, (ii) comparing the one or more panel images to up to each of the plurality of source images of the image dataset, (iii) assigning a diagnostic test article type from a plurality of possible diagnostic test article types, and (iv) returning the diagnostic test article type to the mobile communication device. Each of the results images generally corresponds to one of the diagnostic panels of the diagnostic test article after completing a diagnostic test using the diagnostic test article.

In some embodiments, the method may further comprise combining the one or more results images to the plurality of source images to enhance the image data set.

In some embodiments, the method may further comprise: (i) receiving one of: a manually-changed value or a confirmed value from the mobile communication device, and (ii) storing the one of a manually-changed value or the confirmed value in association with the one or more results images on the one or more network servers, wherein the manually-changed value is different than the automated value, and wherein the confirmed value is the same as the automated value.

Figure 6:
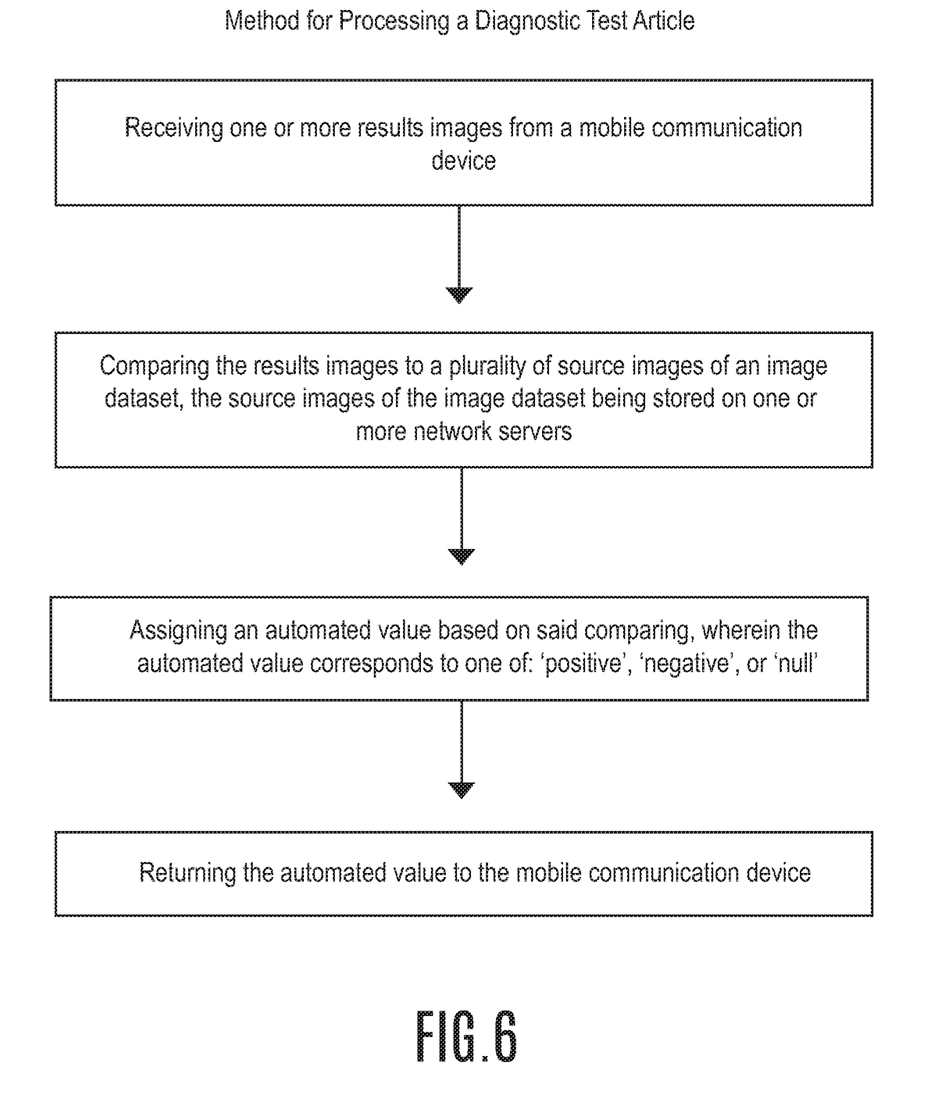
FIG. 6 shows a method for processing a diagnostic test article on a server side of the network infrastructure as shown in FIG. 1 in accordance with yet another embodiment.

FIG. 6 shows a method for processing a diagnostic test article on a server side of the network infrastructure as shown in FIG. 1 in accordance with yet another embodiment. The method is shown comprising: (i) receiving one or more results images from a mobile communication device; (ii) comparing the results images to a plurality of source images of an image dataset, the source images of the image dataset being stored on one or more network servers; (iii) assigning an automated value based on said comparing, wherein the automated value corresponds to one of: 'positive', 'negative', or 'null', and (iv) returning the automated value to the mobile communication device, where the returned value can be presented via the software application. For purposes herein, the term 'null' means a result was unobtainable.

Any range or device value described herein may be extended or altered without losing the effect sought, as will be apparent to the skilled person.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

It will be understood that the benefits and advantages described above may relate to one embodiment or may relate to several embodiments. The embodiments are not limited to those that solve any or all of the stated problems or those that have any or all of the stated benefits and advantages. It will further be understood that reference to 'an' item refers to one or more of those items. One having skill in the art will appreciate that one or more select features or steps of one embodiment may be combined with one or more select features or steps of another embodiment to achieve a system and/or method for processing a diagnostic test article.

The order of execution or performance of the operations in examples of the disclosure illustrated and described herein is not essential, unless otherwise specified. That is, the operations may be performed in any order, unless otherwise specified, and examples of the disclosure may include additional or fewer operations than those disclosed herein. For example, it is contemplated that executing or performing a particular operation before, contemporaneously with, or after another operation is within the scope of aspects of the disclosure.

When introducing elements of aspects of the disclosure or the examples thereof, the articles "a," "an," "the," and "said" are intended to mean that there are one or more of the elements. The terms "comprising," "including," and "having" are intended to be inclusive and mean that there may be additional elements other than the listed elements. The term "exemplary" is intended to mean "an example of." The phrase "one or more of the following: A, B, and C" means "at least one of A and/or at least one of B and/or at least one of C."

Having described aspects of the disclosure in detail, it will be apparent that modifications and variations are possible without departing from the scope of aspects of the disclosure as defined in the appended claims. As various changes could be made in the above constructions, systems, and methods without departing from the scope of aspects of the disclosure, it is intended that all matter contained in the above description and shown in the accompanying drawings shall be interpreted as illustrative and not in a limiting sense.

INDUSTRIAL APPLICABILITY

The invention is useful in the field of medical and substance diagnostic testing.

REFERENCE SIGNS LIST client side (100)
diagnostic test article (110)
mobile communication device (120)
software application (125)
customer side (200)
customer access devices (201; 202)
customer-portion (225)
server side (300)
network servers (301; 302)
server-portion (325)
source images (350)
results panel (355)
internet (400)
internet connections (410*a*; 410*b*; 410*c*)

What is claimed is:

1. A system for processing a diagnostic test article, the system comprising:
   each of a customer side, a client side and a server side connected to internet via one of a plurality of internet connections;
   the customer side including at least one customer access device;
   the client side including a mobile communication device and a client application integrated with the mobile communication device;
   the server side including one or more network servers configured to access an image dataset, the image dataset comprising a plurality of source images;
   characterized in that:
   with the client application, the mobile communication device is configured to execute a series of steps for processing the diagnostic test article, the steps comprising in order:
   (i) identifying a diagnostic test article type from a plurality of possible diagnostic test article types, the diagnostic test article being one of the diagnostic test article types, wherein the diagnostic test article type is associated with characteristic information including: number of diagnostic panels of the diagnostic test article type and number of diagnostic strips for each of the diagnostic panels; and
   (ii) characterizing results of a diagnostic test using the diagnostic test article, wherein said characterizing results comprises:
   acquiring one or more results images, each of the results images corresponding to one of the diagnostic panels of the diagnostic test article,
   comparing each of the one or more results images to a plurality of the source images of the image dataset, and
   for each of the diagnostic strips of the diagnostic panels of the diagnostic test article, assigning an automated value based on said comparing, wherein the automated value corresponds to one of: 'positive', 'negative', or 'null'.

2. The system of claim 1, wherein the client application is integrated with the mobile communication device via the internet.

3. The system of claim 1, wherein the client application is integrated with the mobile communication device via memory housed on the mobile communication device.

4. The system of claim 1, wherein the server side is configured to store a plurality of client records on the one or more network servers, each client record individually comprising test information, wherein the test information includes: the diagnostic test article type, the characteristic information, the automated value for each of the diagnostic strips of the diagnostic panels of the diagnostic test article, the one or more results images, and optionally a client-provided value for one or more of the diagnostic strips of the diagnostic panels.

5. The system of claim 4, further comprising a customer application integrated with the at least one customer access device, wherein the customer application is configured to access the test information associated with one or more of the client records stored on the networks servers.

6. The system of claim 5, wherein the customer application is integrated with the at least one customer access device via the internet.

7. The system of claim 1, wherein the customer application is integrated with the at least one customer access device via memory housed on the at least one customer access device.

8. The system of claim 1, wherein the mobile communication device comprises a smart phone or tablet computer.

9. A method for processing a diagnostic test article, the method comprising, using a client application integrated with a mobile communication device:
   (i) identifying a diagnostic test article type from a plurality of possible diagnostic test article types, the diagnostic test article being one of the diagnostic test article types, wherein the diagnostic test article type is associated with characteristic information including: number of diagnostic panels of the diagnostic test article type and number of diagnostic strips for each of the diagnostic panels; and
   (ii) characterizing results of a diagnostic test using the diagnostic test article, wherein said characterizing results comprises:
   acquiring one or more results images, each of the results images corresponding to one of the diagnostic panels of the diagnostic test article after completing a diagnostic test using the diagnostic test article,
   comparing each of the one or more results images to a plurality of source images of an image dataset, the source images of the image dataset being stored on one or more network servers, and
   for each of the diagnostic strips of the diagnostic panels of the diagnostic test article, receiving from the one or more network servers an automated value based on said comparing, wherein the automated value corresponds to one of: 'positive', 'negative', or 'null'.

10. The method of claim 9, wherein said using a client application integrated with the mobile communication device comprises opening the client application from memory housed on the mobile communication device.

11. The method of claim 9, at least a portion of the client application stored on the one or more network servers, wherein said using a client application integrated with the mobile communication device comprises opening the client application via an internet connection.

12. The method of claim 9, wherein said identifying the diagnostic test article type comprises inputting typographical characters into the client application.

13. The method of claim 9, wherein said identifying the diagnostic test article type comprises using the mobile communication device, scanning a barcode coupled to the diagnostic test article.

14. The method of claim 9, wherein said identifying the diagnostic test article type comprises using the mobile communication device, acquiring one or more panel images of the diagnostic test article, of each panel images corresponding to one of the one or more of the diagnostic panels of the diagnostic test article, comparing the one or more panel images to up to each of the plurality of source images of the image dataset, assigning the diagnostic test article type from a plurality of possible diagnostic test article types, and returning the diagnostic test article type to the mobile communication device.

15. The method of claim 9, wherein said identifying the diagnostic test article type comprises using near-field-communication of the mobile communication device, reading a radiofrequency identification tag coupled to the diagnostic test article.

16. A method for processing a diagnostic test article, the method comprising:
   with one or more network servers connected to a mobile communication device via an internet connection:
      receiving one or more results images from the mobile communication device;
      comparing the results images to a plurality of source images of an image dataset, the source images of the image dataset being stored on the one or more network servers;
      assigning an automated value based on said comparing, wherein the automated value corresponds to one of: 'positive', 'negative', or 'null'; and
      returning the automated value to the mobile communication device;
      receiving from the mobile communication device one or more panel images of the diagnostic test article, each of the panel images corresponding to one of one or more diagnostic panels of the diagnostic test article;
      comparing the one or more panel images to up to each of the plurality of source images of the image dataset;
      assigning a diagnostic test article type from a plurality of possible diagnostic test article types; and
      returning the diagnostic test article type to the mobile communication device.

17. The method of claim 16, wherein each of the results images corresponding to one of the diagnostic panels of the diagnostic test article after completing a diagnostic test using the diagnostic test article.

18. The method of claim 16, further comprising combining the one or more results images to the plurality of source images to enhance the image data set.

19. The method of claim 16, further comprising:
   receiving one of: a manually-changed value or a confirmed value from the mobile communication device, and
   storing the one of a manually-changed value or the confirmed value in association with the one or more results images on the one or more network servers,
   wherein the manually-changed value is different than the automated value, and
   wherein the confirmed value is the same as the automated value.

* * * * *